(12) United States Patent
Otsuka et al.

(10) Patent No.: US 12,322,484 B2
(45) Date of Patent: Jun. 3, 2025

(54) INFORMATION PROCESSING APPARATUS, SKINCARE PRESCRIPTION SYSTEM, SKINCARE PRESCRIPTION METHOD, AND STORAGE MEDIUM

(71) Applicant: CASIO COMPUTER CO., LTD., Tokyo (JP)

(72) Inventors: Toshihiko Otsuka, Ome (JP); Takahiro Tomida, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 375 days.

(21) Appl. No.: 17/898,778

(22) Filed: Aug. 30, 2022

(65) Prior Publication Data
US 2023/0083804 A1    Mar. 16, 2023

(30) Foreign Application Priority Data
Sep. 16, 2021    (JP) .................. 2021-150829

(51) Int. Cl.
  *G16H 20/10*    (2018.01)
  *A61B 5/00*    (2006.01)
  *A61B 5/026*    (2006.01)
  *A61B 5/021*    (2006.01)

(52) U.S. Cl.
  CPC ........... *G16H 20/10* (2018.01); *A61B 5/0261* (2013.01); *A61B 5/4848* (2013.01); *A61B 5/02116* (2013.01)

(58) Field of Classification Search
None
See application file for complete search history.

(56) References Cited

U.S. PATENT DOCUMENTS

| 8,358,348 B2 | 1/2013 | Mohammadi et al. |
| 11,688,068 B2 * | 6/2023 | Gaur ................ G16H 30/40 382/128 |
| 2021/0298620 A1 * | 9/2021 | Otsuka ................ A61B 5/0285 |

FOREIGN PATENT DOCUMENTS

| JP | 2004141259 A | 5/2004 |
| JP | 2013532003 A | 8/2013 |
| JP | 2019025071 A | 2/2019 |

* cited by examiner

*Primary Examiner* — Leon Flores
(74) *Attorney, Agent, or Firm* — Holtz, Holtz & Volek PC

(57) ABSTRACT

An information processing apparatus includes a memory and at least one processor. In the memory, a program is stored. The processor is configured to execute the program stored in the memory, and generate prescription data for skincare of a skin based on history data of an index value representing change in blood flow before and after treatment. The index value is calculated based on a first skin image and a second skin image. The first skin image is obtained by imaging the skin before a blood flow enhancement treatment, and the second skin image is obtained by imaging the skin after the blood flow enhancement treatment.

9 Claims, 8 Drawing Sheets

INFORMATION PROCESSING APPARATUS, SKINCARE PRESCRIPTION SYSTEM, SKINCARE PRESCRIPTION METHOD, AND STORAGE MEDIUM

CROSS-REFERENCE TO RELATED APPLICATIONS

This application is based upon and claims the benefit of priority from Japanese Patent Application No. 2021-150829 filed on Sep. 16, 2021, the entire content of which, including the specification, claims and drawings, is incorporated herein by reference.

BACKGROUND

Technical Field

The present disclosure relates to an information processing apparatus, a skincare prescription system, a skincare prescription method, and a storage medium.

Description of Related Art

There has been known a technique of obtaining blood flow information on the basis of an image obtained by imaging the facial skin of a subject, calculating, on the basis of the obtained blood flow information, skin index values (skin viscoelasticity, water loss, stratum corneum water content, skin color ($a^*$, $b^*$), area of corneocyte, etc.) for evaluating the skin condition of the subject, and proposing a skincare method and/or a skincare product on the basis of the skin index values. There has been also known a technique of obtaining effectiveness information of the skincare method and/or skincare product from the skin index values before and after use of these. (Refer to, for example, JP 2019-25071 A.)

SUMMARY

An information processing apparatus includes:
a memory where a program is stored; and
at least one processor configured to execute the program stored in the memory,
wherein the processor is configured to generate prescription data for skincare of a skin based on history data of an index value representing change in blood flow before and after treatment, the index value being calculated based on a first skin image obtained by imaging the skin before a blood flow enhancement treatment and a second skin image obtained by imaging the skin after the blood flow enhancement treatment.

BRIEF DESCRIPTION OF DRAWINGS

The accompanying drawings, which are incorporated in and constitute a part of the specification, illustrate embodiments, and together with the general description given above and the detailed description of the embodiments given below, serve to explain the principles of the present disclosure, wherein.

DETAILED DESCRIPTION

Hereinafter, an embodiment(s) for carrying out the present disclosure will be described with reference to the drawings. Although various limitations technically preferable for carrying out the present disclosure are put on the embodiment(s) described below, the technical scope of the present disclosure is not limited to the embodiment(s) below or illustrated examples.

[Configuration of Skincare Prescription System 100]

Figure 1:
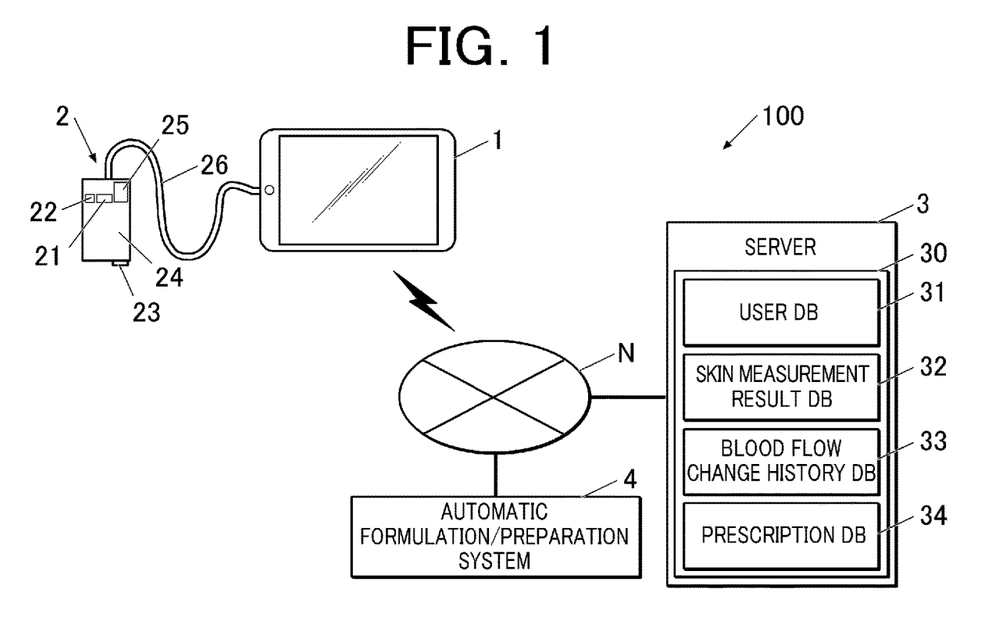
FIG. 1 shows an example of the overall configuration of a skincare prescription system.

FIG. 1 shows an example of the overall configuration of a skincare prescription system 100 according to the present disclosure.

As shown in FIG. 1, the skincare prescription system 100 includes an information processing apparatus 1 to which a measuring sensor 2 is connected, a server 3, and an automatic formulation/preparation system 4. These apparatuses are connected to one another via a communication network N, such as a wide area network (WAN) or the Internet, to exchange data.

The number of information processing apparatuses 1 is not limited to one but may be more than one.

The information processing apparatus 1 calculates/obtains an index value(s) representing change in blood flow before and after treatment (blood flow change index(es)) on the basis of skin image data obtained by the measuring sensor 2 before treatment for enhancing blood flow (blood flow enhancement treatment) (first skin image), such as massage, and skin image data obtained by the measuring sensor 2 after the blood flow enhancement treatment (second skin image), and generates and outputs prescription data for skincare at the timing of determining, on the basis of history data of the index value(s), that the blood flow of skin is in an activated state. Hereinafter, treatment indicates treatment for enhancing blood flow.

The information processing apparatus 1 is not particularly limited in configuration, and may be a tablet terminal, a smartphone, a personal computer (PC) or the like with an application dedicated to skin improvement installed, may be a beauty device provided with a mirror, such as a smart mirror, or may be integrated with the measuring sensor 2, for example.

Figure 2:
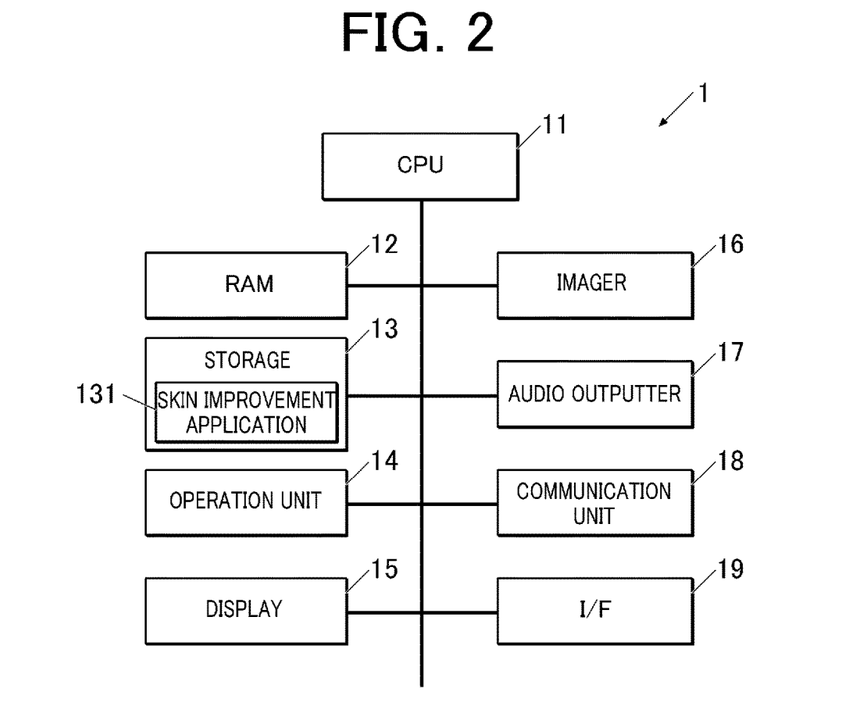
FIG. 2 is a block diagram showing a functional configuration of an information processing apparatus shown in FIG. 1.

FIG. 2 is a block diagram showing a functional configuration of the information processing apparatus 1.

As shown in FIG. 2, the information processing apparatus 1 includes at least one central processing unit (CPU) 11, a random access memory (RAM) 12, a storage 13 as at least one memory, an operation unit 14, a display 15, an imager 16, an audio outputter 17, a communication unit 18, and an interface (I/F) 19. These components are connected to one another by a bus.

The CPU 11 is a processor that performs centralized control of the components of the information processing apparatus 1 by reading programs and data stored in the storage 13 and using the RAM 12 as a work area. For example, the CPU 11 performs a skin improvement process, which is described below, by working together with a skin improvement application 131 stored in the storage 13, and functions as a calculator and a generator.

The RAM 12 forms a temporary storage area for programs, input/output data, parameters and so forth in various processes that are performed and controlled by the CPU 11.

The storage 13 includes a nonvolatile semiconductor memory, a hard disk memory, a read only memory (ROM) and/or the like, and stores various programs, data used in the programs, and so forth.

In this embodiment, the skin improvement application 131 is stored in the storage 13. The skin improvement application 131 is a program for the CPU 11 to perform the below-described skin improvement process. The skin improvement application 131 is downloadable from the server 3, for example.

The operation unit 14 includes, for a user to do various settings or the like, operation buttons and a touchscreen on the display 15, and outputs pieces of operation information corresponding to operations made on the operation buttons and the touchscreen to the CPU 11.

The display 15 includes a liquid crystal display (LCD), an electroluminescence (EL) display or the like, and displays various pieces of display information in accordance with instructions from the CPU 11.

The imager 16 includes an imaging lens, an imaging device, such as a charge coupled device (CCD) image sensor or a complementary metal-oxide semiconductor (CMOS) image sensor, and an analog-to-digital (A/D) converter, and converts an optical image having passed through the imaging lens into two-dimensional image signals with the imaging device to obtain image data (red (R), green (G), blue (B) luminance signals).

The audio outputter 17 includes an audio/speech synthesizer, a digital-to-analog (D/A) converter, an amplifier and a speaker, and synthesizes and outputs audio under the control of the CPU 11.

The communication unit 18 performs communication control to communicate with external apparatuses, such as the server 3 and the automatic formulation/preparation system 4, via the communication network N.

The I/F 19 is an interface to which external apparatuses, such as the measuring sensor 2, are connected for data communication. The information processing apparatus 1 and the measuring sensor 2 may be configured to perform data communication by wireless communication.

The measuring sensor 2 is a cylindrical sensor that measures user's skin condition, and includes an imager 21, an illuminator 22, a semiconductor sensor 23, a cover 24, a controller 25 and an I/F 26.

The imager 21 includes an imaging lens directed toward the tip of the cylindrical cover 24, an imaging device and an A/D converter, and converts an optical image having passed through the imaging lens into two-dimensional image signals with the imaging device to obtain image data (R, G, B luminance signals).

The illuminator 22 includes a light-emitting diode (LED) and a dimmer circuit, and projects light to the field of view of the imager 21.

The semiconductor sensor 23 is a capacitive semiconductor sensor, and disposed at the tip of the cover 24. The semiconductor sensor 23 includes, for example, a plurality of capacitor elements two-dimensionally arranged, and obtains a capacitance value of each capacitor element when the semiconductor sensor 23 is brought into contact with a measurement target (user's skin).

The cover 24 is cylindrical and isolates the imager 21 and the illuminator 22 disposed in the cover 24 from the outside. With the tip of the cover 24 put on the measurement target (user's skin), the illuminator 22 emits light and the imager 21 images the measurement target. By doing so, image data (skin image data) can be obtained with brightness inside the cover 24 kept constant and with influence of disturbance reduced or eliminated.

The controller 25 performs centralized control of the components of the measuring sensor 2.

For example, under the control of the information processing apparatus 1, the controller 25 causes the illuminator 22 to emit light and the imager 21 to perform imaging to obtain image data, and outputs the obtained image data to the information processing apparatus 1 via the I/F 26. Also, under the control of the information processing apparatus 1, the controller 25 causes the semiconductor sensor 23 to perform measurement to obtain the capacitance value of each capacitor element, calculates, from the obtained capacitance value of each capacitor element, an oil content and a moisture content of the measurement target, and outputs data of the oil content and the moisture content (moisture-content and oil-content data) to the information processing apparatus 1 via the I/F 26. As the method for calculating the oil content and the moisture content of the measurement target from the capacitance value of each capacitor element obtained by the semiconductor sensor 23, a method disclosed in JP 2004-141259 A may be used, for example.

The measuring sensor 2 is not limited to the one described above in configuration. For example, the oil content may be obtained by an optical sensor.

The server 3 includes a storage 30, a CPU, a RAM, an operation unit, a display and a communication unit. The storage 30 of the server 3 includes a user database (DB) 31, a skin measurement result DB 32, a blood flow change history DB 33 and a prescription DB 34. The server 3 associates and stores (saves), in the storage 30, skin measurement data, history data of a blood flow change index(es) and prescription data transmitted from the information processing apparatus 1 with a user ID.

The user DB 31 stores user information (user ID, authentication information, name, age, sex, address, telephone number, email address, etc.) of each user who uses the skincare prescription system 100. Examples of the authentication information include a password, facial information, and biometric information, such as fingerprint information. Any of these is usable as the authentication information. In this embodiment, the password is used.

The skin measurement result DB 32 stores, regarding each user, skin measurement data associated with a user ID and date and time of the obtainment.

The blood flow change history DB 33 stores, regarding each user, history data of offset values and history data of PA values (detailed below), which are used in the index values representing change in blood flow of user' skin before and after treatment.

The prescription DB 34 stores, regarding each user, prescription data for a skincare agent(s) associated with a user ID and date and time of the prescription.

The skin improvement application 131 is stored in the storage 30 of the server 3, and the server 3 transmits the skin improvement application 131 to the information processing apparatus 1 in response to a request from the information processing apparatus 1.

The automatic formulation/preparation system 4 includes a not-shown control device and a not-shown automatic formulation/preparation device. The control device of the automatic formulation/preparation system 4 receives, from the information processing apparatus 1, prescription data for a skincare agent(s) and information on a destination to which the skincare agent is to be delivered, and causes the automatic formulation/preparation device to prepare a skincare agent(s) based on the received prescription data, and arranges for and manages delivery of the prepared skincare agent. The automatic formulation/preparation device automatically prepares a skincare agent(s) on the basis of prescription data input from the control device.

[Operation of Skincare Prescription System 100]

Next, operation of the skincare prescription system 100 will be described.

Figure 3:
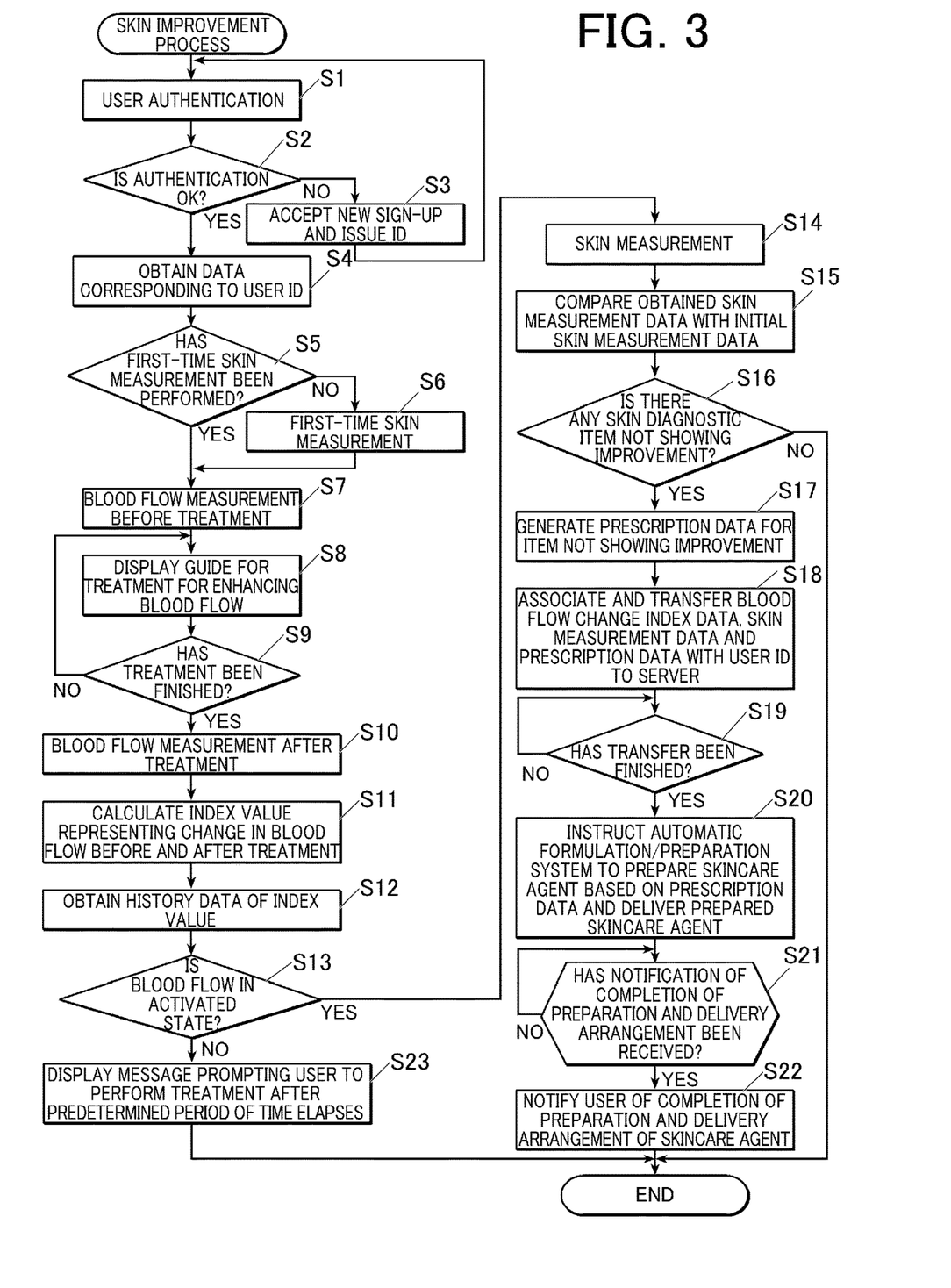
FIG. 3 is a flowchart showing the flow of a skin improvement process that is performed by a CPU shown in FIG. 2.

FIG. 3 is a flowchart showing the flow of the skin improvement process that is performed by the information processing apparatus 1. The skin improvement process is performed by the CPU 11 working together with the skin improvement application 131 stored in the storage 13 when, with the operation unit 14, the skin improvement application 131 is started and an instruction to perform the skin improvement process is issued.

First, the CPU 11 performs user authentication (Step S1).

For example, the CPU 11 causes the display 15 to displays a login screen and transmits, to the server 3, a user ID and a password input by a user on the login screen with the operation unit 14. The server 3 compares the received user ID and password with user information in the user DB 31. If they match, the server 3 notifies the information processing apparatus 1 that the authentication is OK. If they do not match, the server 3 notifies the information processing apparatus 1 that the authentication is NG.

Next, the CPU 11 determines whether the authentication is OK on the basis of a notification from the server 3 (Step S2).

If the authentication is NG (Step S2; NO), the CPU 11 accepts a new sign-up and issues a user ID (Step S3), and returns to Step S1.

In Step S3, for example, the CPU 11 causes the display 15 to display a new sign-up screen to accept (receive) input of user information from the user with the operation unit 14. When user information is input on the new sign-up screen, the CPU 11 transmits the input user information to the server 3 via the communication unit 18 and requests a new sign-up. When the server 3 receives the new sign-up request to register the user information from the information processing apparatus 1, the server 3 issues a user ID and notifies the information processing apparatus 1 of the issued user ID, and also associates and stores the user ID with the received user information in the user DB 31. When the CPU 11 receives the user ID, the CPU 11 causes the display 15 to display a notification of completion of the sign-up and the user ID.

If the authentication is OK (Step S2; YES), the CPU 11 obtains, from the server 3, user information and, if any, initial skin measurement data and history data of a blood flow change index(es) corresponding to the authenticated user ID (Step S4), and proceeds to Step S5.

In Step S5, the CPU 11 determines whether first-time skin measurement has been performed (Step S5). For example, if the CPU 11 obtains the initial skin measurement data from the server 3, the CPU 11 determines that the first-time skin measurement has been performed.

If the CPU 11 determines that the first-time skin measurement has been performed (Step S5; YES), the CPU 11 proceeds to Step S7.

If the CPU 11 determines that the first-time skin measurement has not been performed (Step S5; NO), the CPU 11 performs the first-time skin measurement with the measuring sensor 2 and stores the obtained initial skin measurement data in the RAM 12, and also associates and transmits the initial skin measurement data with the user ID to the server 3 via the communication unit 18 (Step S6), and proceeds to Step S7.

In Step S6, the CPU 11 causes the display 15, the audio outputter 17 and/or the like to output, for example, a message of "For skin measurement, put measuring sensor 2 here." and an image in which a predetermined part of a face (e.g., a point on a cheek, a point under an eye, etc.) is pointed in order to get the user to put the tip of the cover 24 of the measuring sensor 2 on the predetermined part of his/her face, and obtains skin image data and moisture-content and oil-content data from the measuring sensor 2. Then, from the obtained skin image data and moisture-content and oil-content data, the CPU 11 obtains measurement values of predetermined skin diagnostic items (in this embodiment, color density of dark circles under eyes, the number of pores, moisture content, oil content, the number of wrinkles, the number of blotches, and skin tone), and treats the obtained measurement values as the initial skin measurement data. The color density of dark circles under eyes, the number of pores, the number of wrinkles, the number of blotches and the skin tone are obtained by analyzing the skin image data. As a method for analyzing the skin image data to obtain the number of pores, the number of wrinkles and the number of blotches, for example, a method disclosed in JP 2007-152084 A may be used. As a method for analyzing the skin image data to obtain the color density of dark circles under eyes and the skin tone, for example, a method of using a lightness value(s) L* by converting R, G, B luminance values, as which converted luminance (converted luminance values) described below is used in this embodiment, of skin image data into the CIELAB color space (L*a*b*) may be used. However, the methods are not limited to these.

In Step S7, the CPU 11 performs blood flow measurement before treatment (Step S7).

In Step S7, the CPU 11 causes the display 15, the audio outputter 17 and/or the like to output, for example, a message of "For blood flow measurement before treatment, put measuring sensor 2 here and wait." and an image in which a predetermined part of a face (e.g., a point on a cheek, a point under an eye, etc.) is pointed in order to get the user to put the tip of the cover 24 of the measuring sensor 2 on the predetermined part of his/her face, and obtains skin image data (first skin image, e.g., moving image data for a predetermined period of time (e.g., 60 sec.)). When the CPU 11 finishes obtaining the skin image data, the CPU 11 causes the display 15, the audio outputter 17 and/or the like to output, for example, a message of "Measurement Finished". Then, the CPU 11 analyzes the skin image data and calculates, as index values representing blood flow of skin before treatment, an offset value that represents blood volume(s) of skin and a pulse amplitude (PA) value that represents pulse wave amplitude(s) of skin.

The offset value is a representative value of values that are obtained by subtracting R luminance values from G luminance values of the respective frame images in the obtained skin image data (moving image data). The R luminance values are each a representative value of R luminance values (converted luminance) of all the pixels of a frame image in the skin image data. The G luminance values are each a representative value of G luminance values (converted luminance) of all the pixels of a frame image in the skin image data.

The PA value is a representative value of amplitudes of waves (of a waveform) representing temporal change in G luminance value in the obtained skin image data (moving image data). The G luminance value is a representative value of G luminance values (converted luminance) of all the pixels in the skin image data.

The wavelength of green (G) is generally in a range of 495-570 nm, and hemoglobin has a high absorption coefficient at around 500-600 nm. As the blood volume under the skin surface is greater, the amount of hemoglobin is greater and accordingly a greater amount of green light is absorbed by hemoglobin. Hence, as the blood flow of the user's skin is better and accordingly the blood volume is greater, the G luminance value is lower.

In this embodiment, in order to easily and intuitively grasp increase in blood flow, a conversion process is performed to make the luminance value higher as the blood volume increases (is greater). More specifically, in a case where an image sensor of 8-bit output for each of R, G, B colors is used to detect luminance values, a numerical value obtained by subtracting a luminance value detected by the image sensor from the maximum luminance value of 255 is the abovementioned "converted luminance", and this converted luminance is used as a luminance value. Hereinafter, luminance values indicate converted luminance (values).

The G luminance value(s) represents the blood volume(s) of skin. By subtracting R luminance values from G luminance values, noise due to natural light, camera shake and so forth can be reduced or eliminated. Hence, in this embodiment, as one of the index values representing blood flow, the offset value is used, the offset value being a representative value of values obtained by subtracting R luminance values from G luminance values of the respective frame images in the skin image data.

Figure 4:
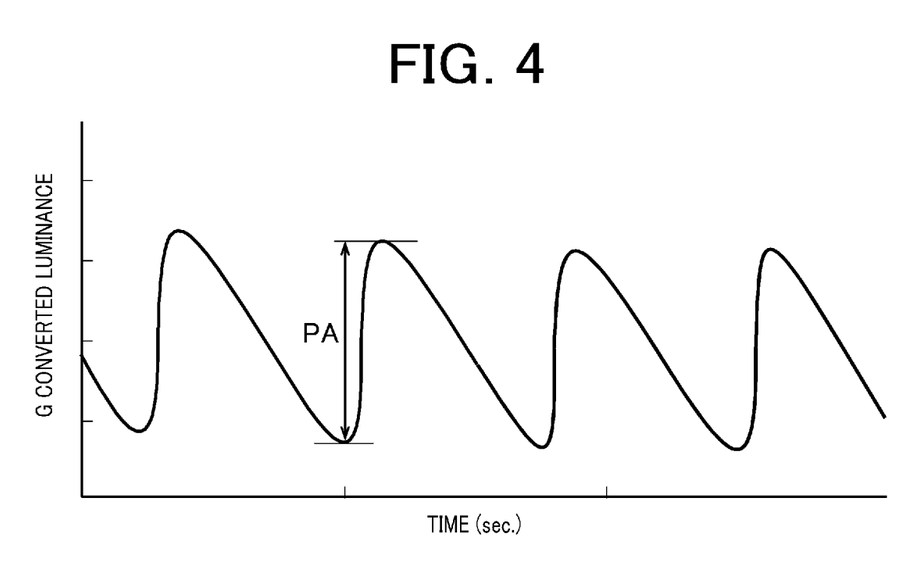
FIG. 4 is an illustration to explain a pulse wave amplitude.

The temporal change in G luminance value, which represents the blood volume, is represented by a waveform as shown in FIG. 4. Each wave of the waveform represents a pulse wave, and the pulse wave amplitude (difference between adjacent maximum and minimum of pulse wave signal, PA), which is the amplitude of each pulse wave, represents strength of pulsation that pumps out blood (facilitates blood flow). Hence, in this embodiment, as one of the index values representing blood flow, the PA value is used, the PA value being a representative value of amplitudes of waves (pulse wave amplitudes) (of a waveform) representing temporal change in G luminance value in the skin image data. If an abnormal value exceeding a preset threshold value is detected in the amplitudes of waves, the abnormal value may be excluded in calculating the representative value.

Examples of the representative value include the mean, median, mode, maximum and minimum. In this embodiment, the mean is used.

Next, the CPU 11 causes the display 15 to display a guide for treatment for enhancing blood flow of skin in order to get the user to perform the treatment (Step S8).

For example, as the guide for the treatment for enhancing blood flow of skin, the CPU 11 causes the display 15 to display a facial animation showing a massage method or to sequentially display, on a facial image, arrows or the like indicating, for example, areas and directions where and in which massage is to be performed. Additionally, the CPU 11 may cause the audio outputter 17 to output an audio guide for the massage method.

Examples of the treatment for enhancing blood flow of skin include massage, application of a blood flow enhancement cream, physical therapy, relaxation, and facial muscle training.

Next, the CPU 11 determines whether the user has input, with the operation unit 14, an operation indicating that he/she has finished the treatment (Step S9).

If the CPU 11 determines that the user has input the operation indicating that he/she has finished the treatment (Step S9; YES), the CPU 11 performs blood flow measurement after treatment (Step S10).

The process in Step S10 is the same as that in Step S7 described above, except that, in the message to be output, "before treatment" is replaced by "after treatment", and hence its description will be omitted.

Next, the CPU 11 calculates the index value(s) representing change in blood flow before and after treatment (Step S11).

FIG. 5A to FIG. 5D each show temporal changes in R, G, B luminance values in skin image data before or after massage as the treatment.

Figure 5A:
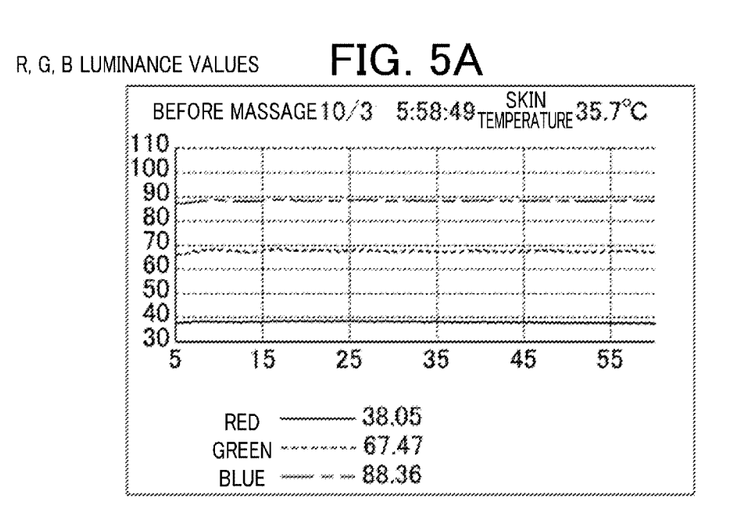
FIG. 5A shows temporal changes in R, G, B luminance values before massage.
Figure 5B:
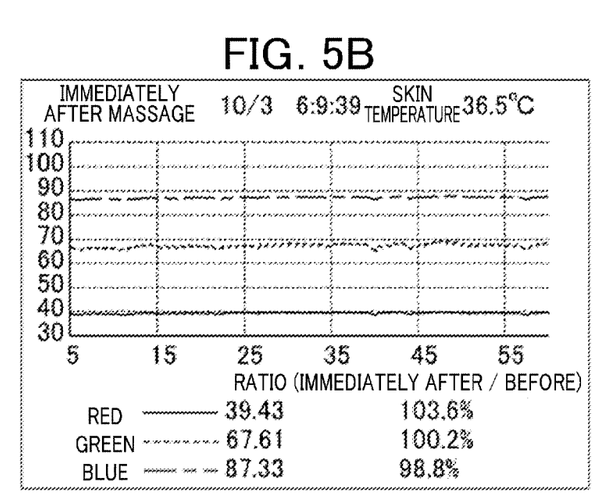
FIG. 5B shows temporal changes in R, G, B luminance values after massage on the same day as that of FIG. 5A.
Figure 5C:
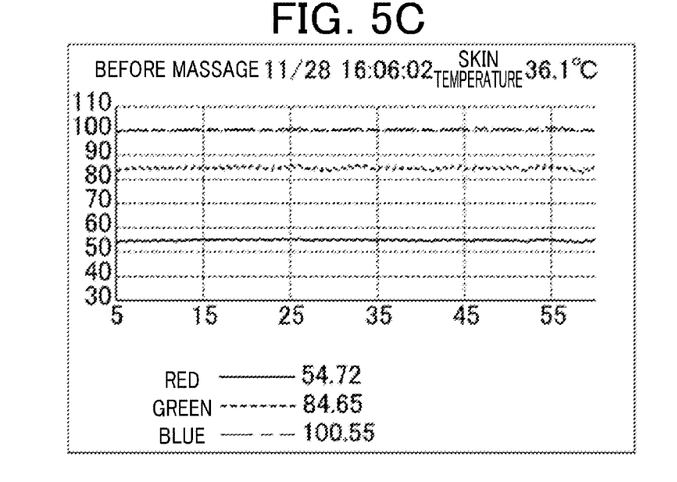
FIG. 5C shows temporal changes in R, G, B luminance values before massage on a day about two months after the day of FIG. 5A and FIG. 5B.
Figure 5D:
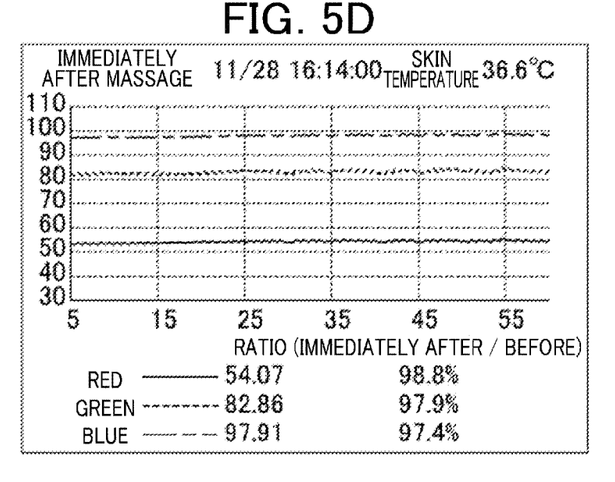
FIG. 5D shows temporal changes in R, G, B luminance values after massage on the same day as that of FIG. 5C.
Figure 6A:
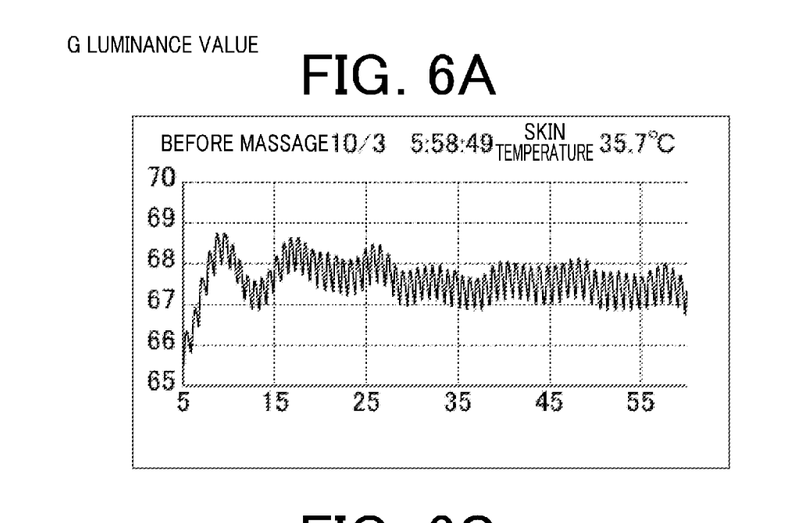
FIG. 6A is a graph showing only the temporal change in G luminance value extracted from the temporal changes in R, G, B luminance values shown in FIG. 5A with the vertical axis enlarged.
Figure 6B:
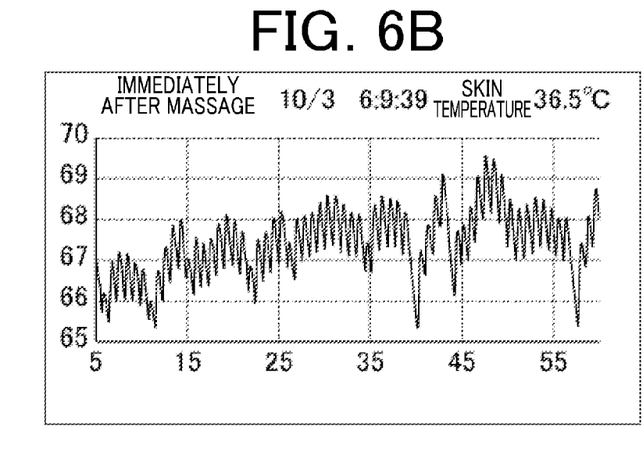
FIG. 6B is a graph showing only the temporal change in G luminance value extracted from the temporal changes in R, G, B luminance values shown in FIG. 5B with the vertical axis enlarged.
Figure 6C:
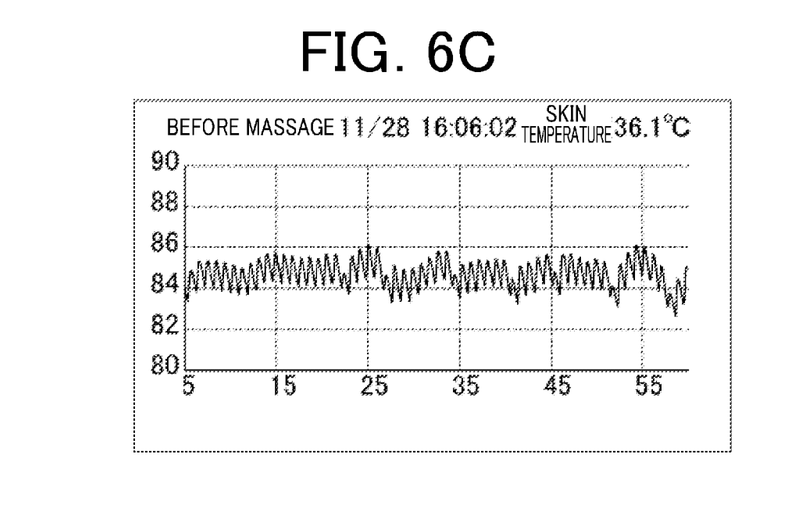
FIG. 6C is a graph showing only the temporal change in G luminance value extracted from the temporal changes in R, G, B luminance values shown in FIG. 5C with the vertical axis enlarged.
Figure 6D:
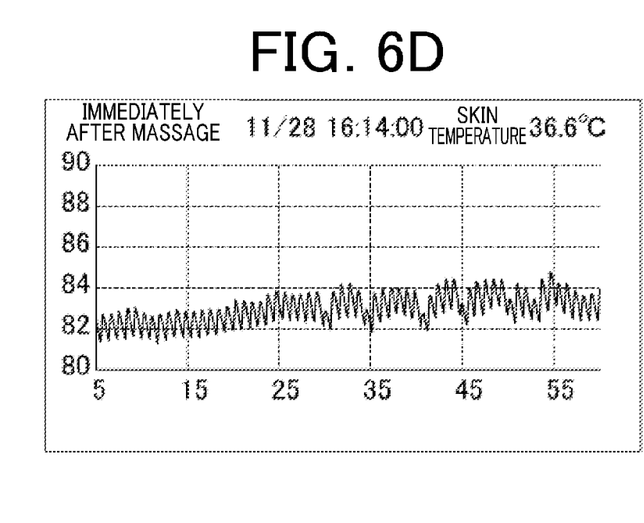
FIG. 6D is a graph showing only the temporal change in G luminance value extracted from the temporal changes in R, G, B luminance values shown in FIG. 5D with the vertical axis enlarged.

More specifically, for example, FIG. 5A shows temporal changes in pre-massage R, G, B luminance values on October 3, FIG. 5B shows temporal changes in post-massage R, G, B luminance values on the same day, namely, October 3, FIG. 5C shows temporal changes in pre-massage R, G, B luminance values on November 28 about two months after the day of FIG. 5A and FIG. 5B, and FIG. 5D shows temporal changes in post-massage R, G, B luminance values on the same day, namely, November 28.

The R, G, B luminance values in each graph show temporal changes in the means of luminance values of R, G, B signals of all the pixels in skin image data.

FIG. 6A to FIG. 6D each show only the temporal change in G luminance value extracted from the temporal changes in R, G, B luminance values shown in their respective FIG. 5A to FIG. 5D with the vertical axis enlarged. FIG. 6A, FIG. 6B, FIG. 6C and FIG. 6D correspond to FIG. 5A, FIG. 5B, FIG. 5C and FIG. 5D, respectively.

FIG. 7A to FIG. 7D each show, in order to reduce or eliminate influence of disturbance, temporal change in G-R luminance value obtained by subtracting the temporal change in R luminance value from the temporal change in G luminance value shown in their respective FIG. 5A to FIG. 5D with the vertical axis enlarged. The mean of the temporal change in G-R luminance value shown in each of FIG. 7A to FIG. 7D is the offset value described above. FIG. 7A, FIG. 7B, FIG. 7C and FIG. 7D correspond to FIG. 5A and FIG. 6A, FIG. 5B and FIG. 6B, FIG. 5C and FIG. 6C, and FIG. 5D and FIG. 6D, respectively.

FIG. 8A to FIG. 8D each show temporal change in pulse wave amplitude before or after massage as the treatment. The pulse wave amplitude shown in each of FIG. 8A to FIG. 8D is the amplitude of each wave of the waveform representing the temporal change in G luminance value shown in each of FIG. 6A to FIG. 6D. The mean of the temporal change shown in each of FIG. 8A to FIG. 8D is the PA value described above. FIG. 8A, FIG. 8B, FIG. 8C and FIG. 8D correspond to FIG. 6A, FIG. 6B, FIG. 6C and FIG. 6D, respectively.

Figure 7A:
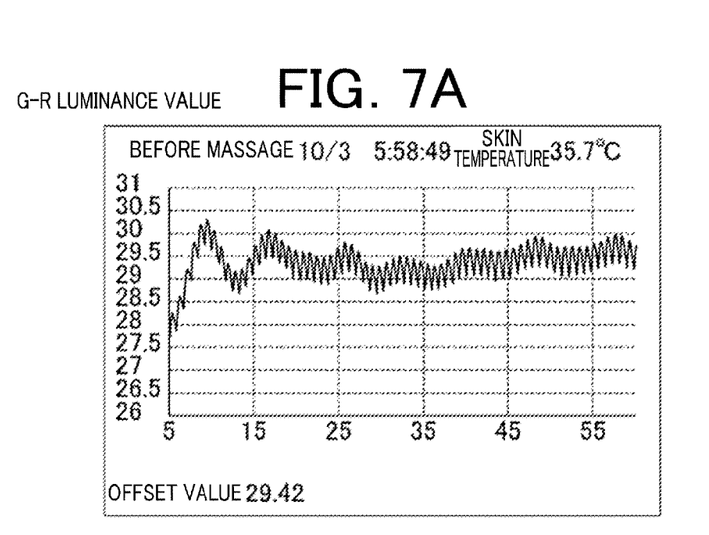
FIG. 7A is a graph showing temporal change in G-R luminance value obtained by subtracting the temporal change in R luminance value shown in FIG. 5A from the temporal change in G luminance value shown in FIG. 5A with the vertical axis enlarged.
Figure 7B:
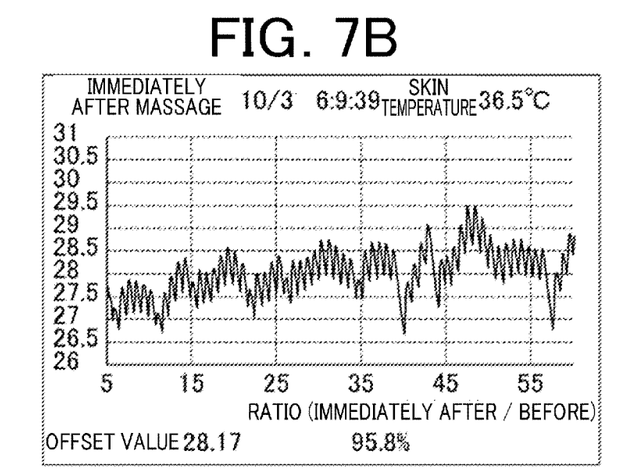
FIG. 7B is a graph showing temporal change in G-R luminance value obtained by subtracting the temporal change in R luminance value shown in FIG. 5B from the temporal change in G luminance value shown in FIG. 5B with the vertical axis enlarged.
Figure 7C:
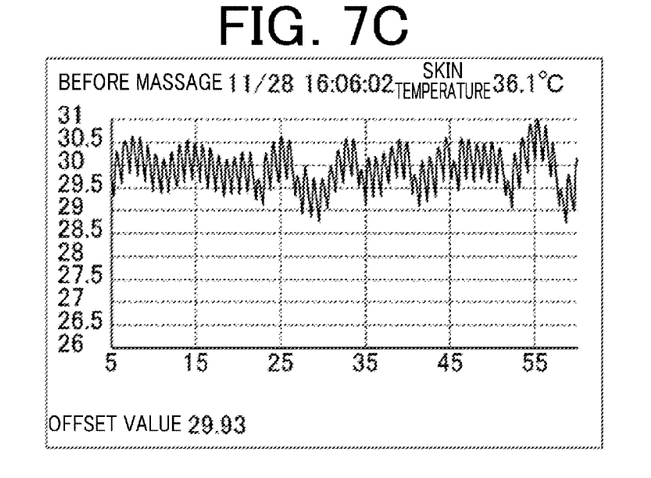
FIG. 7C is a graph showing temporal change in G-R luminance value obtained by subtracting the temporal change in R luminance value shown in FIG. 5C from the temporal change in G luminance value shown in FIG. 5C with the vertical axis enlarged.
Figure 7D:
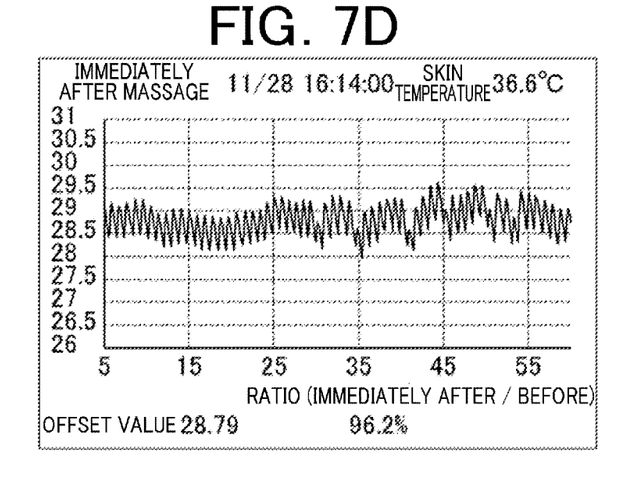
FIG. 7D is a graph showing temporal change in G-R luminance value obtained by subtracting the temporal change in R luminance value shown in FIG. 5D from the temporal change in G luminance value shown in FIG. 5D with the vertical axis enlarged.
Figure 8A:
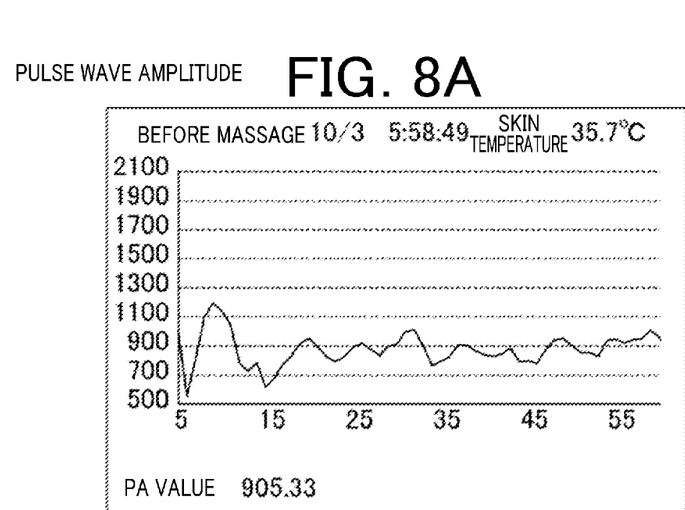
FIG. 8A is a graph showing temporal change in pulse wave amplitude before massage, corresponding to FIG. 6A.
Figure 8B:
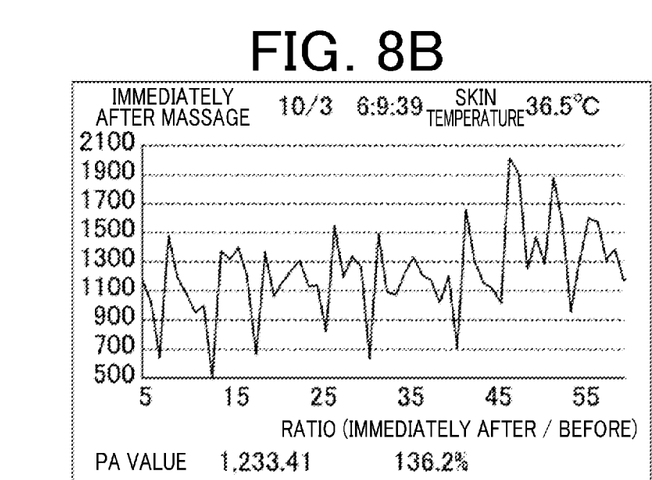
FIG. 8B is a graph showing temporal change in pulse wave amplitude after massage, corresponding to FIG. 6B.
Figure 8C:
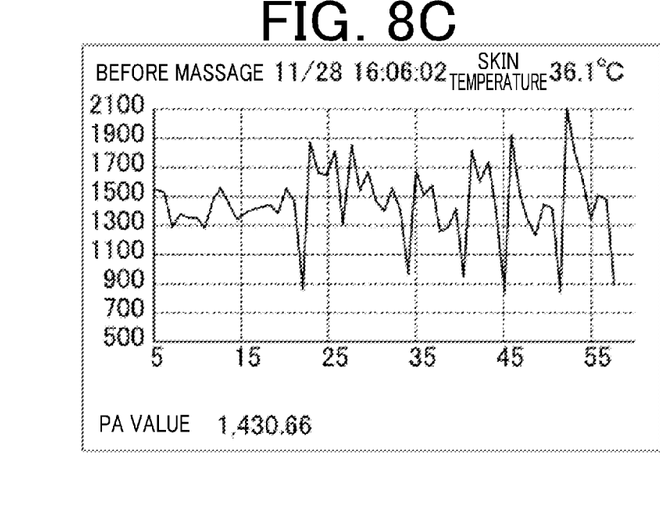
FIG. 8C is a graph showing temporal change in pulse wave amplitude before massage, corresponding to FIG. 6C.
Figure 8D:
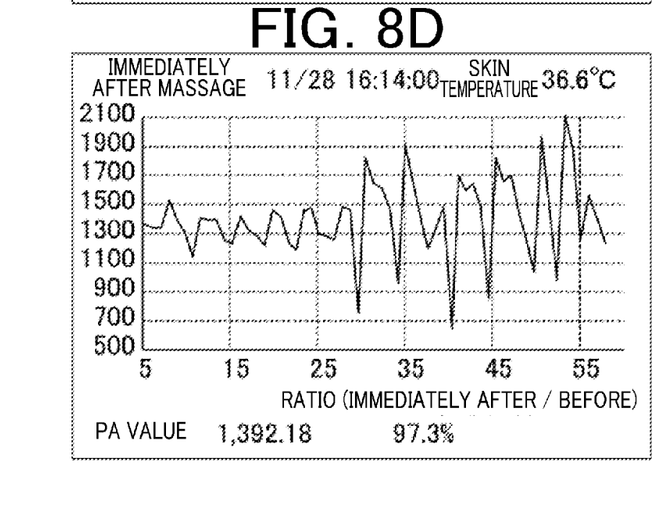
FIG. 8D is a graph showing temporal change in pulse wave amplitude after massage, corresponding to FIG. 6D.

In Step S11, for example, as the index value(s) representing change in blood flow before and after treatment, the CPU 11 calculates (i) a ratio (percentage) obtained by dividing the offset value that is the mean of the temporal change in post-massage G-R luminance value shown in FIG. 7B or FIG. 7D by the offset value that is the mean of the temporal change in pre-massage G-R luminance value shown in FIG. 7A or FIG. 7C and/or (ii) a ratio (percentage) obtained by dividing the PA value that is the mean of the temporal change in post-massage pulse wave amplitude shown in FIG. 8B or FIG. 8D by the PA value that is the mean of the temporal change in pre-massage pulse wave amplitude shown in FIG. 8A or FIG. 8C.

The index value representing change in blood flow before and after treatment is not limited to a ratio (percentage), but, for example, a rate of change if it represents change in offset value or PA value before and after treatment.

When the CPU 11 calculates the index value(s) representing change in blood flow before and after treatment, the CPU 11 obtains history data of the index value representing change in blood flow before and after treatment (including the index value calculated this time) (Step S12), and determines on the basis of the history data whether the blood flow of the skin is in the activated state (i.e., whether the blood flow stays activated) (Step S13).

If the blood flow of skin is sluggish, oxygen and nutrients necessary for skin do not sufficiently spread, and the skin cell turnover (cell cycle) is disrupted (slows down). This causes dead corneocyte, which normally peels off in 28 days, to stay in the skin, so that the skin become thicker. This prevents ingredients of skincare agents from reaching deep into skin, so that a sufficient effect of skin improvement is not obtained.

Hence, in this embodiment, the CPU 11 determines whether (the blood flow of) the skin is in the activated state, and prescribes and delivers a skincare agent(s) at the timing of determining that the skin is in the activated state. This enables provision of skincare agents at the timing at which a sufficient effect of skin improvement is obtained from skincare agents.

Figure 9:
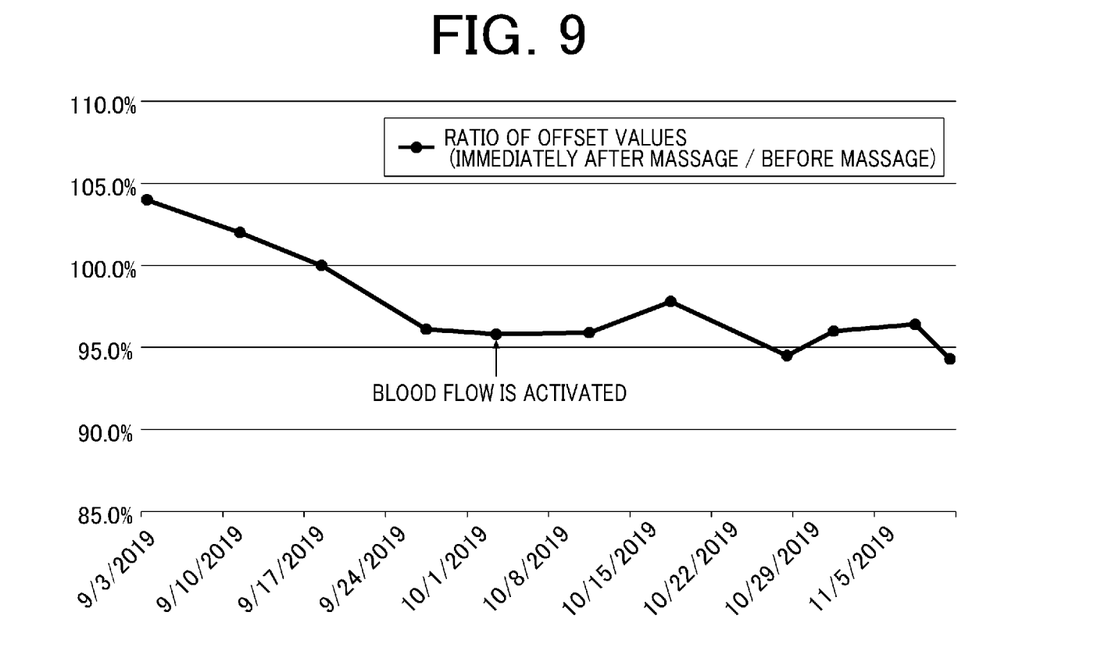
FIG. 9 is a graph showing change in ratio of offset values before and after massage (post-massage offset value/pre-massage offset value)

FIG. 9 is a graph showing change in ratio of offset values before and after massage (post-massage offset value/pre-massage offset value) in a case where massage has been continued over a long period of time, namely, a graph of history data of the ratio of offset values before and after treatment.

As shown in FIG. 9, at the beginning of the long-term massage, the ratio of the post-massage offset value to the pre-massage offset value is high (the post-massage offset value is greater than the pre-massage offset value), but as the days go by from the start of the long-term massage, the ratio of the post-massage offset value to the pre-massage offset value gradually decreases, and, in the end, changes little and remains nearly constant.

This is because, at the beginning of the long-term massage, the blood flow is improved by massage, so that the blood volume after massage shows a great increase, but while massage is repeatedly performed, the blood flow stays activated even before massage, so that the change in blood volume steadies.

Hence, the CPU 11 determines, for example, on the basis of the history data of the ratio of offset values before and after treatment, whether the ratio of offset values before and after treatment remains nearly constant (e.g., whether the fluctuation of the ratio from the last-time ratio is within a predetermined range), and if the CPU 11 determines that the ratio remains nearly constant, determines that the blood flow is in the activated state. For example, at and after a point of time indicated by an arrow in the graph shown in FIG. 9, it is determined that the blood flow is in the activated state.

Figure 10:
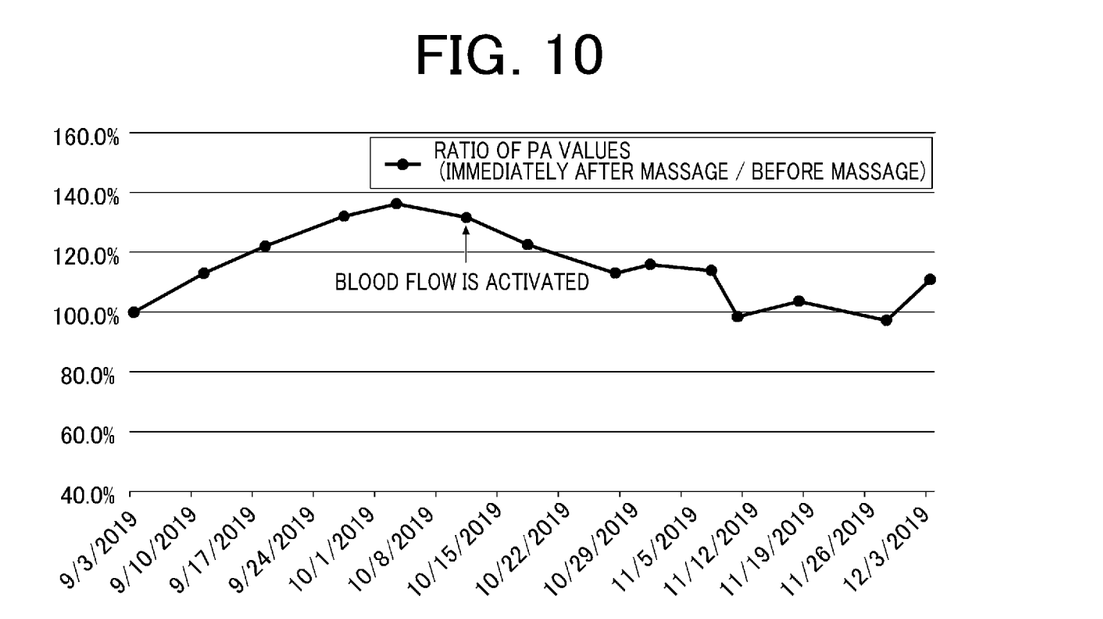
FIG. 10 is a graph showing change in ratio of PA values before and after massage (post-massage PA value/pre-massage PA value).

FIG. 10 is a graph showing change in ratio of PA values before and after massage (post-massage PA value/pre-massage PA value) in a case where massage has been continued over a long period of time, namely, a graph of history data of the ratio of PA values before and after treatment.

As shown in FIG. 10, as to PA values, at the beginning of the long-term massage, as the days go by, the ratio of the post-massage PA value to the pre-massage PA value increases, but eventually reaches the peak, and thereafter gradually decreases to and hovers around 100% (i.e., the change in PA value before and after massage is small).

This is because, at the beginning of the long-term massage, capillaries are dilated by external pressure of massage, so that the blood flow after massage shows an increase due to pulsation, but while massage is repeatedly performed, the capillaries stay dilated, so that the change in pulse wave amplitude before and after massage decreases.

Hence, the CPU 11 determines, for example, on the basis of the history data of the ratio of PA values before and after treatment, whether the ratio of PA values before and after treatment has taken a downward turn, and if the CPU 11 determines that the ratio has taken a downward turn, determines that the blood flow is in the activated state. For example, at and after a point of time indicated by an arrow in the graph shown in FIG. 10, it is determined that the blood flow is in the activated state.

In Step S13, the CPU 11 may determine whether the blood flow is in the activated state on the basis of both the history data of the ratio of offset values before and after treatment and the history data of the ratio of PA values before and after treatment, or either one of the history data. For example, as to a person whose blood flow is good from the beginning, the ratio of offset values before and after treatment does not change. In such a case, it is preferable to determine whether the blood flow is in the activated state using only the history data of the ratio of PA values.

If the CPU 11 determines that the blood flow is not in the activated state (Step S13; NO), the CPU 11 causes the display 15 or the audio outputter 17 to output a message prompting the user to start the skin improvement application and perform the treatment again after a predetermined period of time elapses (e.g., 24 hours later) (Step S23), and ends the skin improvement process.

If the CPU 11 determines that the blood flow is in the activated state (Step S13; YES), the CPU 11 performs skin measurement with the measuring sensor 2 and obtains skin measurement data (Step S14).

In Step S14, the CPU 11 performs the same process as that in Step S6 (but data transmission is unnecessary) and obtains skin measurement data of the same skin diagnostic items as those of the initial skin measurement data obtained in Step S6.

Next, the CPU 11 compares the skin measurement data obtained in Step S14 with the initial skin measurement data (Step S15), and determines whether there is any skin diagnostic item not showing improvement (Step S16).

If any of the inequalities below holds, the CPU 11 determines that there is at least one skin diagnostic item not showing improvement, wherein the initial values represent the measurement values of the respective skin diagnostic items in the initial skin measurement data, and the measurement values a represent the measurement values of the respective skin diagnostic items in the skin measurement data obtained in Step S14. If the initial value and the measurement value a of a skin diagnostic item satisfies the inequality for the skin diagnostic item, the skin diagnostic item is determined as a skin diagnostic item not showing improvement (unimproved skin diagnostic item).

Color Density of Dark Circles under Eyes: Measurement Value a>Initial Value
Number of Pores: Measurement Value a>Initial Value
Oil Content: Measurement Value a<Initial Value
Moisture Content: Measurement Value a<Initial Value
Number of Wrinkles: Measurement Value a>Initial Value
Number of Blotches: Measurement Value a>Initial Value
Skin Tone: Measurement Value a>Initial Value If the CPU 11 determines that there is at least one skin diagnostic item not showing improvement (Step S16; YES), the CPU 11 generates prescription data for a skincare agent(s) to improve the item(s) not showing improvement (Step S17).

For example, the storage 13 stores a table where the ingredient(s) and the amount (e.g., proper amount for the measurement value a) of a skincare agent(s) to be prescribed are stored for each skin diagnostic item, and the CPU 11 generates prescription data for a skincare agent(s) on the basis of the skin improvement item(s) not showing improvement and the table.

If the color density of dark circles under eyes has not improved, a skincare agent having an effect of blood flow enhancement is prescribed. If the number of pores has not improved, a facial cleanser is prescribed. If the oil content and/or the moisture content have not improved, a skincare agent containing a moisturizing ingredient(s) (glycerin, propylene glycol, etc.) is prescribed. If the number of wrinkles and/or the number of blotches have not improved, a skincare agent containing a UV protective ingredient(s) (histidine, tyrosine, tryptophan, urocanic acid, etc.) is prescribed. If the skin tone has not improved, a skincare agent containing a skin-lightening ingredient(s) (e.g., hydroquinone, vitamin C derivative, kojic acid, arbutin, etc.) is prescribed. If two or more items, except the number of pores, show no improvement, preparation/generation of one skincare agent in which ingredients suitable for the items concerned are mixed may be prescribed.

In Step S15, instead of comparing the measurement values a with their respective initial values, the CPU 11 may compare the measurement values a with their respective predetermined threshold values for determining whether there is any skin diagnostic item not showing improvement. Examples of the threshold value(s) include: the mean of measurement values of persons whose ages are the same as (or similar to) the age of the user (current logged-in user); and the mean of measurement values in, among skin-type groups generated by machine learning or the like using initial skin measurement data of persons, a skin-type group as which the user is classified by machine learning or the like using the initial skin measurement data of the user. Alternatively, the CPU 11 may compare the measurement values a with their respective measurement values in skin measurement data obtained last time.

Next, the CPU 11 associates and transfers the obtained blood flow change index data, skin measurement data and prescription data with the user ID to the server 3 via the communication unit 18 (Step S18).

The server 3 stores the received blood flow change index data, skin measurement data and prescription data in the blood flow change history DB 33, the skin measurement result DB 32 and the prescription DB 34, respectively.

When the CPU 11 finishes transferring the data (Step S19; YES), the CPU 11 transmits (outputs), to the automatic formulation/preparation system 4 via the communication unit 18, the prescription data and information on a destination (e.g., name, address, etc. included in the user information) to which a skincare agent(s) is to be delivered, and instructs the automatic formulation/preparation system 4 to prepare a skincare agent(s) based on the prescription data and deliver the skincare agent to the destination (Step S20).

When the control device of the automatic formulation/preparation system 4 receives the prescription data and the information on the destination from the information processing apparatus 1, the control device outputs the prescription data to the automatic formulation/preparation device and causes the automatic formulation/preparation device to prepare a skincare agent(s) based on the prescription data, and also arranges for delivery of the skincare agent on the basis of the information on the destination, and when completing the delivery arrangement, notifies the information processing apparatus 1 of that.

When the CPU 11 receives a notification of the completion of preparation and delivery arrangement of the skincare agent from the automatic formulation/preparation system 4 via the communication unit 18 (Step S21; YES), the CPU 11 notifies the user of the completion of preparation and delivery arrangement of the skincare agent (Step S22), and ends the skin improvement process.

In Step S22, for example, the CPU 11 causes the display 15 of the information processing apparatus 1 to display a notification of the completion of delivery arrangement of the skincare agent, or may send the notification of the completion of delivery arrangement of the skincare agent to the user's email address or the like.

As described above, the CPU 11 of the information processing apparatus 1 obtains history data of an index value(s) representing change in blood flow before and after treatment, the index value being calculated based on a first skin image obtained by imaging skin before the blood flow enhancement treatment and a second skin image obtained by imaging the skin after the blood flow enhancement treatment, and generates and outputs prescription data for skincare based on the obtained history data.

This enables prescription for skincare at the timing at which a sufficient effect of skin improvement is obtained, on the basis of the history data of the index value representing change in blood flow before and after the blood flow enhancement treatment.

For example, the CPU 11 determines, based on the history data of the index value representing change in blood flow before and after treatment, whether the blood flow of the skin is in the activated state, and generates and outputs the prescription data for skincare in response to determining that the blood flow of the skin is in the activated state.

This enables prescription for skincare at the timing at which the blood flow of skin is in the activated state and a sufficient effect of skin improvement is obtained.

For example, the CPU 11 calculates, as the index value representing change in blood flow before and after treatment, an index value representing change in pulse wave amplitude before and after treatment, and generates and outputs the prescription data in response to detecting, based on the history data of the index value representing change in pulse wave amplitude before and after treatment, that the index value representing change in pulse wave amplitude before and after treatment has taken a downward turn.

This enables prescription for skincare at the timing at which the blood flow of skin is in the activated state and a sufficient effect of skin improvement is obtained.

Alternatively or additionally, for example, the CPU 11 calculates, as the index value representing change in blood flow before and after treatment, an index value representing change in blood volume before and after treatment, and generates and outputs the prescription data in response to detecting, based on the history data of the index value representing change in blood volume before and after treatment, that the fluctuation of the index value representing change in blood volume before and after treatment is within a predetermined range.

This enables prescription for skincare at the timing at which the blood flow of skin is in the activated state and a sufficient effect of skin improvement is obtained.

Further, for example, the CPU 11 makes a diagnosis on the skin based on skin measurement data obtained by measuring the skin, and generates and outputs the prescription data based on the result of the diagnosis on the skin.

This enables generation and output of the optimum prescription data based on a skin diagnosis result.

Further, the prescription data includes prescription data for a skincare agent to be applied to the skin. This enables prescription of skincare agents at the timing at which a sufficient effect of skin improvement is obtained.

Further, the CPU 11 transmits, to a predetermined destination, such as the automatic formulation/preparation system 4, instruction information on preparation of the skincare agent based on the prescription data and delivery of the skincare agent. This enables issuance of instructions on preparation and delivery of prescribed skincare agents.

Those described in the above embodiment(s) are not limitations but some of preferred examples of the information processing apparatus, the skincare prescription system, the skincare prescription method and the storage medium storing the program(s) according to the present disclosure.

For example, some or all of the processes (steps) of the skin improvement process performed by the CPU 11 of the information processing apparatus 1 in the above embodiment may be performed by another processor(s), such as the CPU of the server 3. That is, another processor(s), such as the CPU of the server 3, may be provided with some or all of the functions of the information processing apparatus 1, such as the functions as the calculator and the generator.

As an example, the skin image data and the moisture-content and oil-content data obtained by the measuring sensor 2 may be transmitted to the server 3, and the server 3 may calculate the measurement values of the skin diagnostic items. As another example, the skin image data before and after treatment obtained by the measuring sensor 2 may be transmitted to the server 3, and the server 3 may calculate the index value(s) representing change in blood flow before and after treatment, determine whether the blood flow is in the activated state on the basis of the history data of the index value(s) representing change in blood flow before and after treatment, and/or generate the prescription data.

Further, for example, the information processing apparatus 1 may be provided with the functions and/or the various databases that the server 3 of the skincare prescription system 100 has.

Further, in the above embodiment, the measuring sensor 2 is used to obtain the skin image data, but the imager 16 of the information processing apparatus 1 may be used to obtain the skin image data. In the case where the measuring sensor 2 is used to obtain the skin image data, the information processing apparatus 1 may not have the imager 16.

Further, in the above embodiment, on the basis of the history data of the index value(s) representing change in blood flow before and after treatment, prescription data for a skincare agent(s) suitable for a skin diagnostic item(s) not showing improvement is generated, but the prescription data to be generated thereon may be prescription data for a massage method for skincare or prescription data for physical therapy to be performed therefor.

Further, in the above embodiment, as the luminance values for calculating the index value(s) representing change in blood flow before and after treatment, the converted luminance (values) is used, but the skin improvement process may be performed using the detected luminance values themselves without the conversion process.

Further, in the above embodiment, the automatic formulation/preparation device automatically prepares a skincare agent(s) on the basis of the prescription data, but a person may prepare a skincare agent(s) on the basis of the prescription data.

Further, in the above embodiment, the instruction(s) on preparation of a skincare agent(s) based on the prescription data and delivery of the skincare agent is transmitted to the automatic formulation/preparation system 4, but the preparation instruction and the delivery instruction may be transmitted to different destinations. Further, instruction information on the preparation only or instruction information on the delivery only may be transmitted to a predetermined destination.

Further, in the above embodiment, the ROM or the like is used as the computer-readable storage medium storing the program(s) according to the present disclosure, but the computer-readable storage medium is not limited thereto. The computer-readable storage medium may be a hard disk, an SSD, or a portable storage medium, such as a CD-ROM. Further, as a medium to provide data of the program(s) according to the present disclosure via a communication line, a carrier wave may be used.

Besides, detailed configurations/components and operations of the apparatuses constituting the skincare prescription system can also be appropriately modified without departing from the scope of the present disclosure.

Although one or more embodiments of the present disclosure have been described above, the technical scope of the present disclosure is not limited to the embodiments above, but defined on the basis of claims. Further, the technical scope of the present disclosure also includes equivalents to the claims with changes irrelevant to the essence of the present disclosure made.

What is claimed is:

1. An information processing apparatus comprising:
a memory where a program is stored; and
at least one processor configured to execute the program stored in the memory,
wherein the processor is configured to generate prescription data for skincare of a skin based on history data of an index value representing change in blood flow before and after treatment, the index value being calculated based on a first skin image obtained by imaging the skin before a blood flow enhancement treatment and a second skin image obtained by imaging the skin after the blood flow enhancement treatment,
wherein the index value comprises an index value representing change in pulse wave amplitude before and after treatment from a pulse wave amplitude calculated based on the first skin image to a pulse wave amplitude calculated based on the second skin image, and
wherein the processor is further configured to generate the prescription data in response to detecting based on the history data that the index value representing change in pulse wave amplitude before and after treatment has taken a downward turn.

2. The information processing apparatus according to claim 1, wherein the processor is configured to determine based on the history data whether a blood flow of the skin is in an activated state, and generate the prescription data in response to determining that the blood flow of the skin is in the activated state.

3. The information processing apparatus according to claim 1,
wherein the index value comprises an index value representing change in blood volume before and after treatment from a blood volume calculated based on the first skin image to a blood volume calculated based on the second skin image, and
wherein the processor is configured to generate the prescription data in response to detecting based on the history data that a fluctuation of the index value representing change in blood volume before and after treatment is within a predetermined range.

4. The information processing apparatus according to claim 1, wherein the processor is configured to make a diagnosis on the skin based on measurement data obtained by measuring the skin, and generate the prescription data based on a result of the diagnosis on the skin.

5. The information processing apparatus according to claim 1, wherein the prescription data includes prescription data for a skincare agent to be applied to the skin.

6. The information processing apparatus according to claim 5, wherein the processor is configured to transmit, to a predetermined destination, instruction information on preparation of the skincare agent based on the prescription data and/or delivery of the skincare agent.

7. A skincare prescription system comprising:
at least one processor configured to calculate an index value representing change in blood flow before and after treatment based on a first skin image obtained by imaging a skin before a blood flow enhancement treatment and a second skin image obtained by imaging the skin after the blood flow enhancement treatment; and
a memory where history data of the calculated index value is stored,
wherein the processor is configured to obtain the history data and generate prescription data for skincare of the skin based on the obtained history data,
wherein the index value comprises an index value representing change in pulse wave amplitude before and after treatment from a pulse wave amplitude calculated based on the first skin image to a pulse wave amplitude calculated based on the second skin image, and
wherein the processor is further configured to generate the prescription data in response to detecting based on the history data that the index value representing change in pulse wave amplitude before and after treatment has taken a downward turn.

8. A skincare prescription method that is performed by a computer, comprising:
generating prescription data for skincare of a skin based on history data of an index value representing change in blood flow before and after treatment, the index value being calculated based on a first skin image obtained by imaging the skin before a blood flow enhancement treatment and a second skin image obtained by imaging the skin after the blood flow enhancement treatment,
wherein the index value comprises an index value representing change in pulse wave amplitude before and after treatment from a pulse wave amplitude calculated based on the first skin image to a pulse wave amplitude calculated based on the second skin image, and
wherein the prescription data is generated in response to detecting based on the history data that the index value representing change in pulse wave amplitude before and after treatment has taken a downward turn.

9. A non-transitory computer-readable storage medium storing a program that causes a computer to:
generate prescription data for skincare of a skin based on history data of an index value representing change in blood flow before and after treatment, the index value being calculated based on a first skin image obtained by imaging the skin before a blood flow enhancement treatment and a second skin image obtained by imaging the skin after the blood flow enhancement treatment,
wherein the index value comprises an index value representing change in pulse wave amplitude before and after treatment from a pulse wave amplitude calculated based on the first skin image to a pulse wave amplitude calculated based on the second skin image, and wherein the prescription data is generated in response to detecting based on the history data that the index value representing change in pulse wave amplitude before and after treatment has taken a downward turn.

\* \* \* \* \*